(12) United States Patent
Romanach et al.

(10) Patent No.: US 10,520,400 B1
(45) Date of Patent: Dec. 31, 2019

(54) STREAM SAMPLER—MASS REDUCTION SYSTEM FOR FLOWING POWDERS

(71) Applicants: Rodolfo J. Romanach, Mayaguez, PR (US); Rafael Mendez, Mayaguez, PR (US)

(72) Inventors: Rodolfo J. Romanach, Mayaguez, PR (US); Rafael Mendez, Mayaguez, PR (US)

(73) Assignee: University of Puerto Rico, San Juan, PR (US)

(*) Notice: Subject to any disclaimer, the term of this patent is extended or adjusted under 35 U.S.C. 154(b) by 0 days.

(21) Appl. No.: 16/136,047

(22) Filed: Sep. 19, 2018

Related U.S. Application Data

(60) Provisional application No. 62/560,219, filed on Sep. 19, 2017.

(51) Int. Cl.
*G01N 1/20* (2006.01)
*G01N 21/85* (2006.01)

(52) U.S. Cl.
CPC ............. *G01N 1/2035* (2013.01); *G01N 1/20* (2013.01); *G01N 2021/8592* (2013.01)

(58) Field of Classification Search
CPC .................. G01N 1/2035; G01N 1/20; G01N 2001/2007; G01N 2001/2064; G01N 2001/2071; G01N 21/85; G01N 2021/8592
See application file for complete search history.

(56) References Cited

U.S. PATENT DOCUMENTS

| | | | | |
|---|---|---|---|---|
| 6,418,805 B1* | 7/2002 | Carney | ................ | A01D 41/127 374/142 |
| 7,765,882 B2* | 8/2010 | Greten | .................... | G01N 1/20 366/131 |
| 8,683,878 B2* | 4/2014 | Secord | .................... | G01N 1/04 73/863.41 |
| 8,820,586 B2* | 9/2014 | Ozawa | .................. | B65G 65/46 222/236 |

* cited by examiner

*Primary Examiner* — Justin N Olamit
(74) *Attorney, Agent, or Firm* — Hoglund & Pamias, PSC; Roberto J. Rios

(57) ABSTRACT

A device for obtaining samples from a flowing powder stream and performing their immediate analysis using a spectroscopic method is provided. Systematic sample size reduction is achieved to provide representative samples and their immediate (real-time) analysis. The powder blends may come from pharmaceutical, vitamin and nutraceutical products, which must fulfill blend homogeneity requirements. All parts of the batch will have the same probability of being selected as a sample. Samples are obtained without disturbing or changing the composition of the powder blend during the sampling process. Unlike the sample thief commonly used in the pharmaceutical industry, the device of the invention does not disturb the powder blend and does not change the properties of the powder blend during the sampling.

22 Claims, 10 Drawing Sheets

-Prior Art-

STREAM SAMPLER—MASS REDUCTION SYSTEM FOR FLOWING POWDERS

BACKGROUND OF THE INVENTION

The blending of a drug with excipients is one of the most common unit operations in the manufacture of tablets and capsules. The distribution of the drug throughout the blend should be uniform. The uniformity of drug distribution in the blend is one of the most important parameters to be controlled during a tablet manufacturing process to ensure all manufactured products have the correct amount of pharmaceutical ingredient and all patients receive the expected drug content. Federal regulations (Sections 211.110a, b and c in the Code of Federal Regulations), demands that pharmaceutical manufacturers obtain and test samples from materials of each batch to monitor and validate the performance of their manufacturing processes. Federal regulations require manufacturers to develop specifications for the uniformity of powder blends. All products manufactured must comply with these specifications once they are established. Over the last 20 years the Food and Drug Administration (FDA) evaluated two draft guidance protocols on how to perform powder sampling. The first draft guidance was withdrawn and the second one was never approved. Thus, currently each pharmaceutical needs to develop its own specifications for powder sampling.

Powder sampling is currently performed in the pharmaceutical industry using a sample thief of the prior art as the described on U.S. Pat. No. 5,337,620A and US20110000322A1 and illustrated in FIG. 7. However, these devices are unable to provide information from the entire batch of the powder blend produced. The sample thief extracts material from pre-selected locations within a blender as illustrated in FIG. 8. In this method, the thief is unable to identify poorly blended areas that are not included in these pre-selected locations. Powder samples are obtained from the pre-selected locations and all parts of the batch do not have the same opportunity of being selected. As shown in FIG. 8, a user would have to manually insert the sample thief into a blender inlet port and proceed to push the sample thief until reaching the pre-selected location or locations according to predefined sets of sampling steps. For example, a sample set (1) would require the user to insert the sample thief until reaching the location designated as [A], take the sample and remove the sample thief from the blender. Afterwards, for a sample set (2), the user inserts again the sample thief until reaching locations designated as [B-C-D], take the corresponding sample and remove the sample thief from the blender. As can be appreciated, the current method of the prior art cannot provide information from the entire batch of the powder blend produced (i.e., area outside the preselected locations).

Moreover, the sample thief method requires that operators use a ladder or scaffold to insert a sample thief into the blender and operators must be taller than the blender's height to insert the sample thief. Therefore, operators must bend and insert a stainless steel sample thief which could weigh 20-30 pounds, and pull out material 6-9 feet below the surface, placing significant stress on their backs. Even though the sampling is performed for therapeutic products, extensive exposure to the pharmaceutical blends might harm manufacturing personnel. Moreover, usually not all operators are certified at each company to work with the sample thief due to the difficulty in handling these heavy metal spears.

Furthermore, the sample thief may push material from one layer to another when powder is removed from a blender so the operator must work carefully with the sample thief to avoid mixing powder from the different depths of the blender as illustrated in FIG. 8.

The composition of the powder blend may also be affected by the insertion of the thief into the powder static bed. The sample thief may push down material from the top of a powder bed when inserted, thus affecting the composition of the blend and also causes segregation when particles are attracted electrostatically to the metal rod. The sample thief may also break particles when it is inserted. Thus, the thief often alters the composition of the samples extracted adding significant errors in the sampling process that cannot be corrected (or quantified) and does not provide valuable information on the batch of the powder blend that is being analyzed.

Sampling alternatives have been proposed in the last few years. However, many limitations are present in their design. One of the very first attempts to implement In-line sample acquisition was proposed by Edwin Walter in 1930 (U.S. Pat. No. 1,966,712 A), where a grain sampling device was developed, which was capable of taking samples directly from the grains of a stream in a pipe. Although, this device was able to automatically take samples in different time intervals by using a probe-discharge system actuated by compressed air, the samples were not representative of the lot since the probe was only capable of taking samples from a fraction of the grain stream. Moreover, sample thieves of the prior art are usually limited to a total of 10-12 samples within a blender that may contain 300 kg or more of material.

All sampling procedures in pharmaceutical/vitamins powder applications will include errors due to the sampling procedure and provide inaccurate values of the drug concentration. Estimating the sampling errors is not possible with the currently used sample thieves, since each insertion of the thief will produce a different error, a costly problem that could occur at any time with the presently used sample thief.

Accordingly, there is a need of providing a system and method that overcomes the problems associated with the prior art while obtaining accurate samples without disturbing the powder bed.

SUMMARY OF INVENTION

The present invention obtains a sample without disturbing the powder bed guarantying that all parts of the batch have the same opportunity to be selected as a sample. The invention described here solves the above-explained challenges.

The proposed invention is based on the fundamental powder sampling principles: 1) all parts of the manufactured batch should have the same probability of being sampled, and 2) the composition of the powder blend should not be altered during the sampling process. Accordingly, technology capable of obtaining powder samples from the whole lot without disturbing the original state of the powder is required.

According to one aspect of the invention, a full cross-section of the flowing powder sample is obtained so that all parts of the batch will have the same opportunity of being sampled.

According to another aspect of the invention, a device/system based on the fundamental above-explained principles is proposed to obtain samples from pharmaceutical powder blends while minimizing sampling errors and fulfilling the Food and Drug Administration (FDA) requirements.

According to still another aspect of the invention, a correct sampling protocol is implemented in different stages of the pharmaceutical manufacturing process, reducing variation and error sources.

According to yet another aspect of the invention, the apparatus will determine whether a powder blend remains uniform as it exits a powder blender. The apparatus captures the powder blend as it flows out of a blender. This constitutes a novel improvement over the prior art, since powder blends are not made to remain inside a blender or a powder dryer. Powder blends must flow out of a blender or dryer to be used for pharmaceutical tablets used by millions of patients, or to form the powdered infant formulas that are the main source of nutrition for many children. According to one aspect of the invention, the apparatus provides a method to determine whether the powder flows affects the property of the blend as powder flow could segregate or affect a powder blend.

According to another aspect of the invention, the apparatus is relatively small, portable and could be used to obtain powder blends in diverse industries.

According still another aspect of the invention, the apparatus is not limited to taking samples from pharmaceutical powder blends and can be used to evaluate the manufacture of powdered infant formula, detergent formulations, and in other industries such as but not limited to pharmaceutical industries.

According yet another aspect of the invention, the apparatus allows obtaining multiple samples of the flowing powder stream, wherein samples may be obtained throughout the entire emptying of a powder blender and will not be obtained from the same location always as with the currently used sample thieves. Thus, all parts of the blend will have the same opportunity of being selected.

According to one aspect of the invention, the apparatus allows 1-D sampling where samples are separated along a time scale as the powder exits from the blender. Samples could be obtained every 30 seconds, or every 5 minutes, along a time scale that will vary according to the application.

According to another aspect of the invention, the apparatus provides a way to know the order in which samples are obtained allowing variographic analysis of the data that allows estimating the sampling error. Sampling error estimation makes it possible to discern between the variation in the blend concentration due to the sampling and the variation in the blend concentration to the process itself.

According to an aspect of the invention, Variographic analysis can be performed with the inventive device since powder is flowing and samples are separated along a time scale as the powder exits the blender (1-D sampling) something that is not possible with the current thief sampling methods. The use of variographic analysis improves the powder mixing processes, as the process variation is clearly decoupled from the sampling process eliminating or greatly reducing the possibility that a well-mixed batch of a product could be rejected because of a sampling error. Accordingly, the present invention improves a blending process, ultimately protects patients from receiving a tablet with an over or sub-dose of a drug.

According to still another aspect of the invention, the apparatus allows replicating experiments and establishing specifications for a powder mixture. The specifications may be developed based on a set of criteria for sampling representativeness which are part of a set of best practices for sampling, known as the Theory of Sampling (Danish-Standards-Foundation, 2013).

According to yet another aspect of the invention, the apparatus is also sufficiently small that it could be used to introduce powder blends into powder characterization instruments. The apparatus of the present invention could introduce powder to particle size distribution system to provide valuable information on powder properties.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Figure 1:
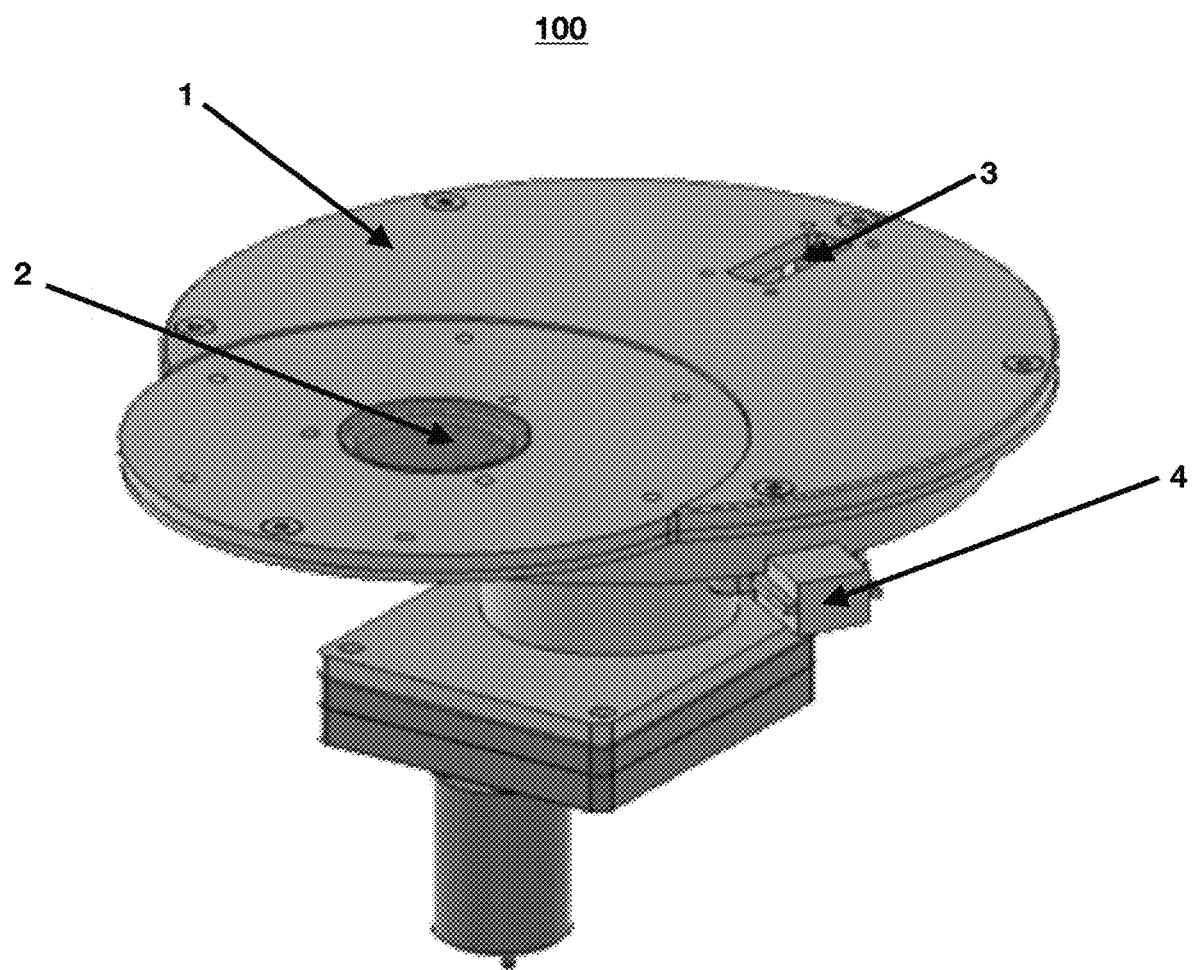
FIG. 1 shows a perspective view of the sampling reduction system according to the present invention.

The present invention provides representative samples of pharmaceutical powder mixtures and their real-time analysis. As shown in FIG. 1, the sampling reduction system comprises a powder sample (100) with a top cover (1) having a sapphire window (2), a preferably rectangular powder inlet (3) and a sampling system (4) that will be discussed in more detailed below. The sapphire window (2) transmits near infrared light, which makes the powder sampler (100) suitable for spectroscopic measurements in this spectral region. Near infrared spectra can be obtained while the powder flows, and the drug concentration can be determined using specialized multivariate analysis software. The rectangular powder inlet (3) is located at a predetermined angular distance from the center of the sapphire window to allow the powder flow phenomena to stabilize before taking spectroscopic measurements. In a preferred embodiment, the rectangular powder inlet (3) is located at about 200 degrees from the center of the sapphire window. Certain distance tolerance and/or deviation are allowed or expected as long as the powder flow is stabilized prior to taking spectroscopic measurements.

Figure 2:
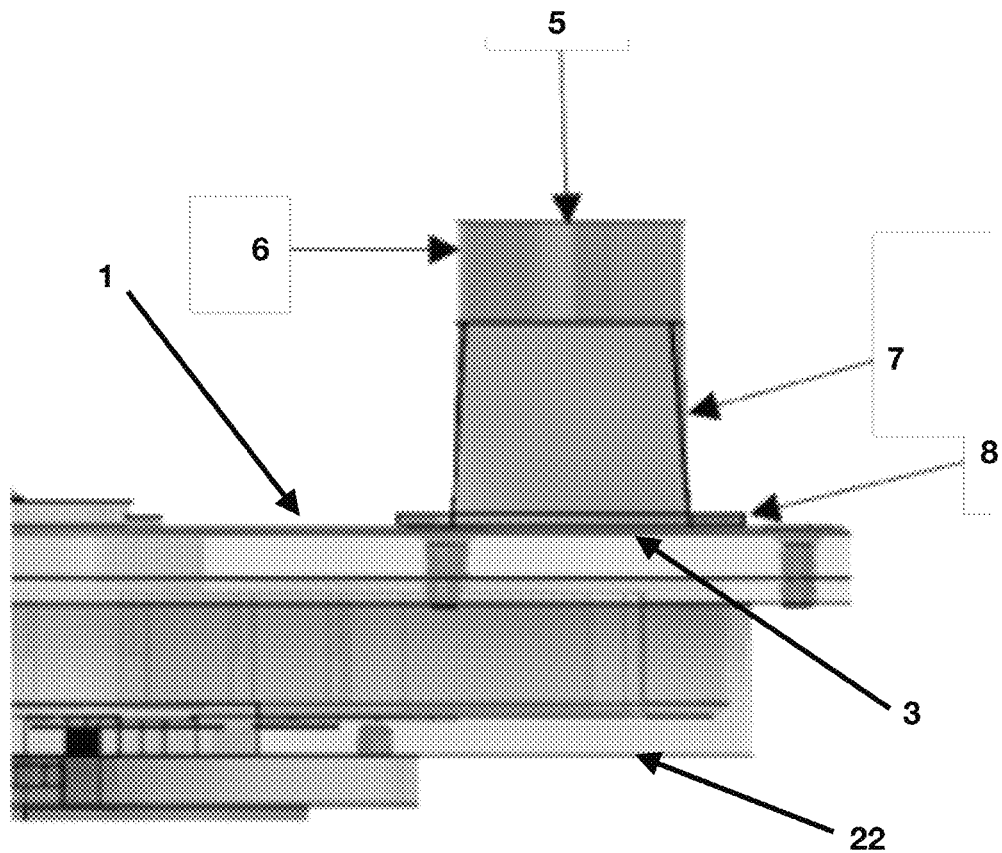
FIG. 2 shows a cross-sectional view of the stream powder inlet according to the present invention.

FIG. 2 shows a powder inlet (5) where the powder will enter the powder sampler. Specifically, the powder inlet (5) has a powder line adapter (6) having a circular geometry, a flexible adapter (7) and an adapter (8) attached to the powder sampler top cover (1) positioned on top of the rectangular powder inlet (3). The circular geometry of the powder line adapter (6) allows connecting the powder sampler to other pipes within the manufacturing area or it can be connected to an additional stage of the sample reduction system. The flexible adapter (7) allows adjusting the powder inlet (5) for different angles of powder flow providing the advantage of connecting the powder sampler to different pipe angles within the manufacturing area. Finally, the powder inlet (5) is connected to the rectangular inlet (3) of the device top cover (1) through an adapter (8).

Figure 3A:
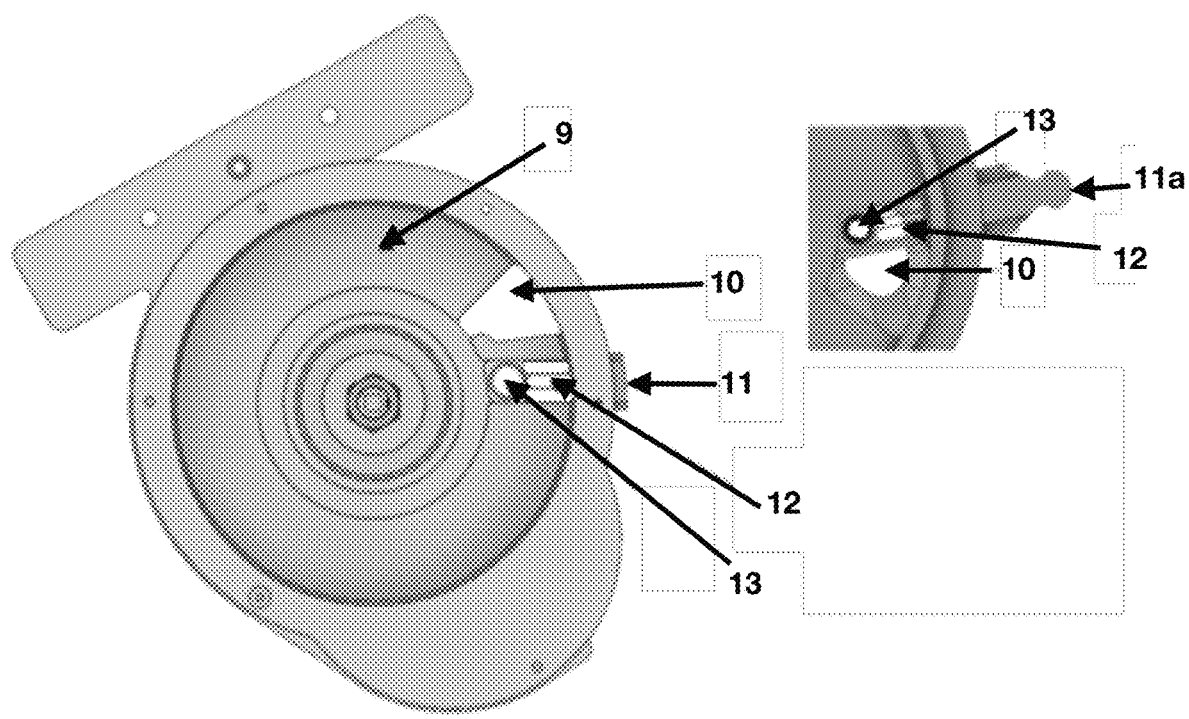
FIG. 3a shows a top view of the powder sampler without the top cover according to the present invention.
Figure 3B:
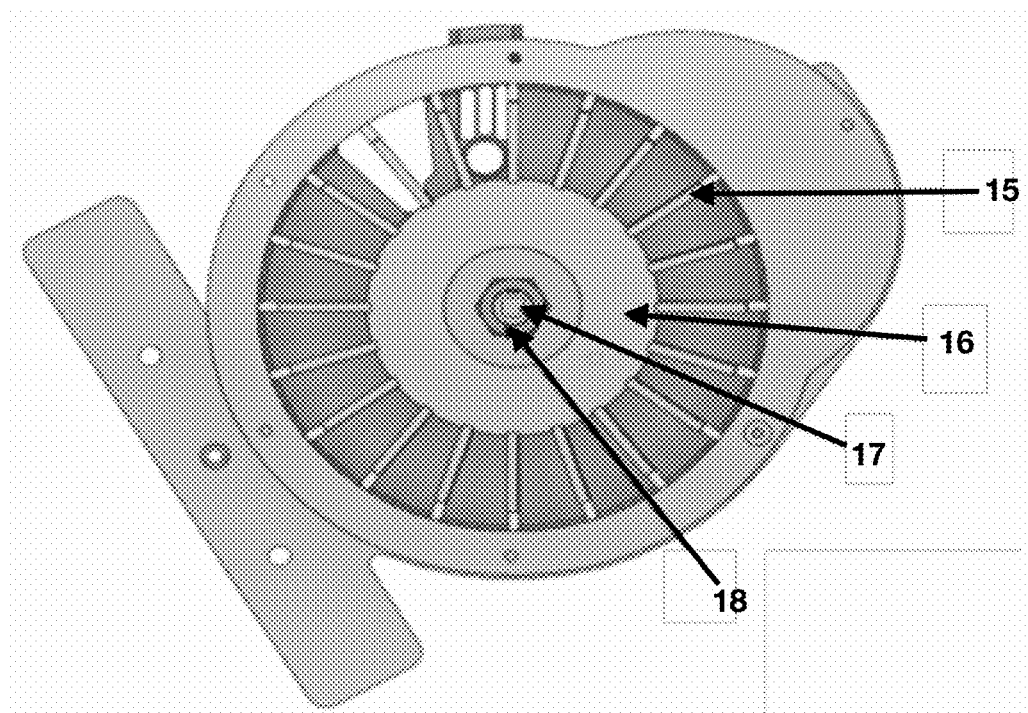
FIG. 3b shows another top view of the sample size reduction system without the top cover including the paddle wheel according to the present invention.
Figure 4:
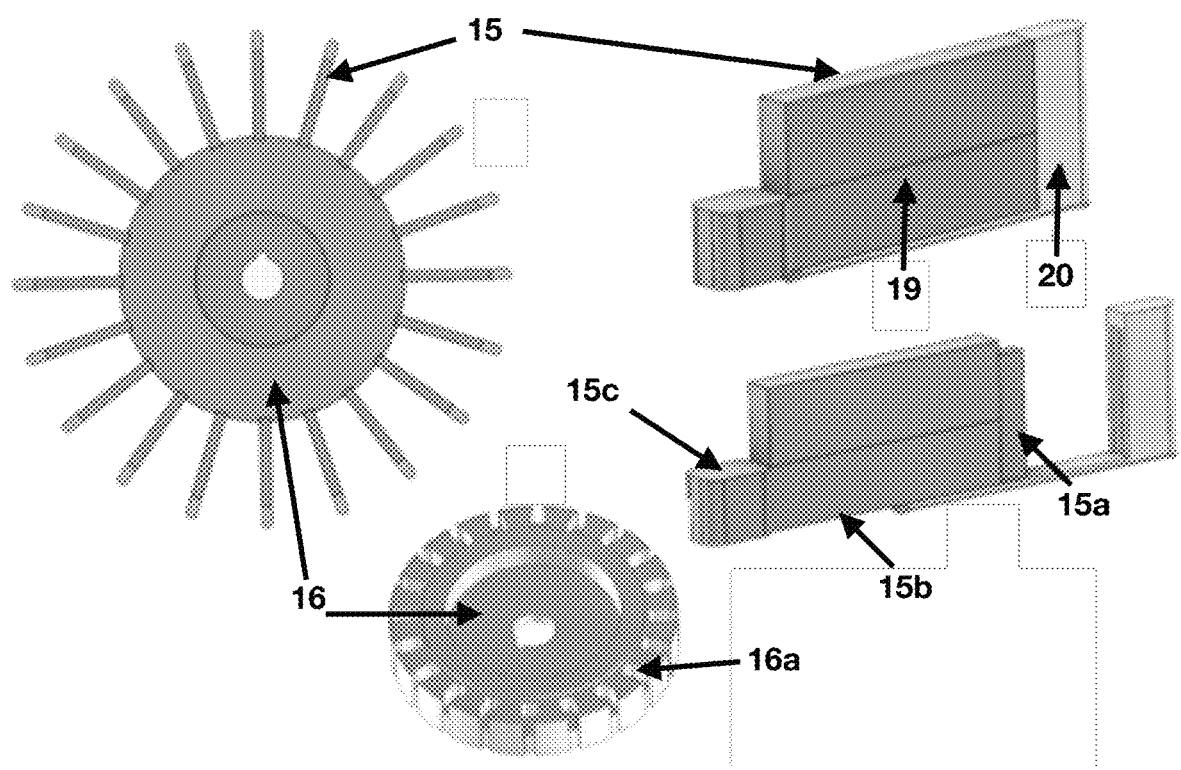
FIG. 4 shows a detailed view of the powder sampler paddle wheel according to the present invention.
Figure 6:
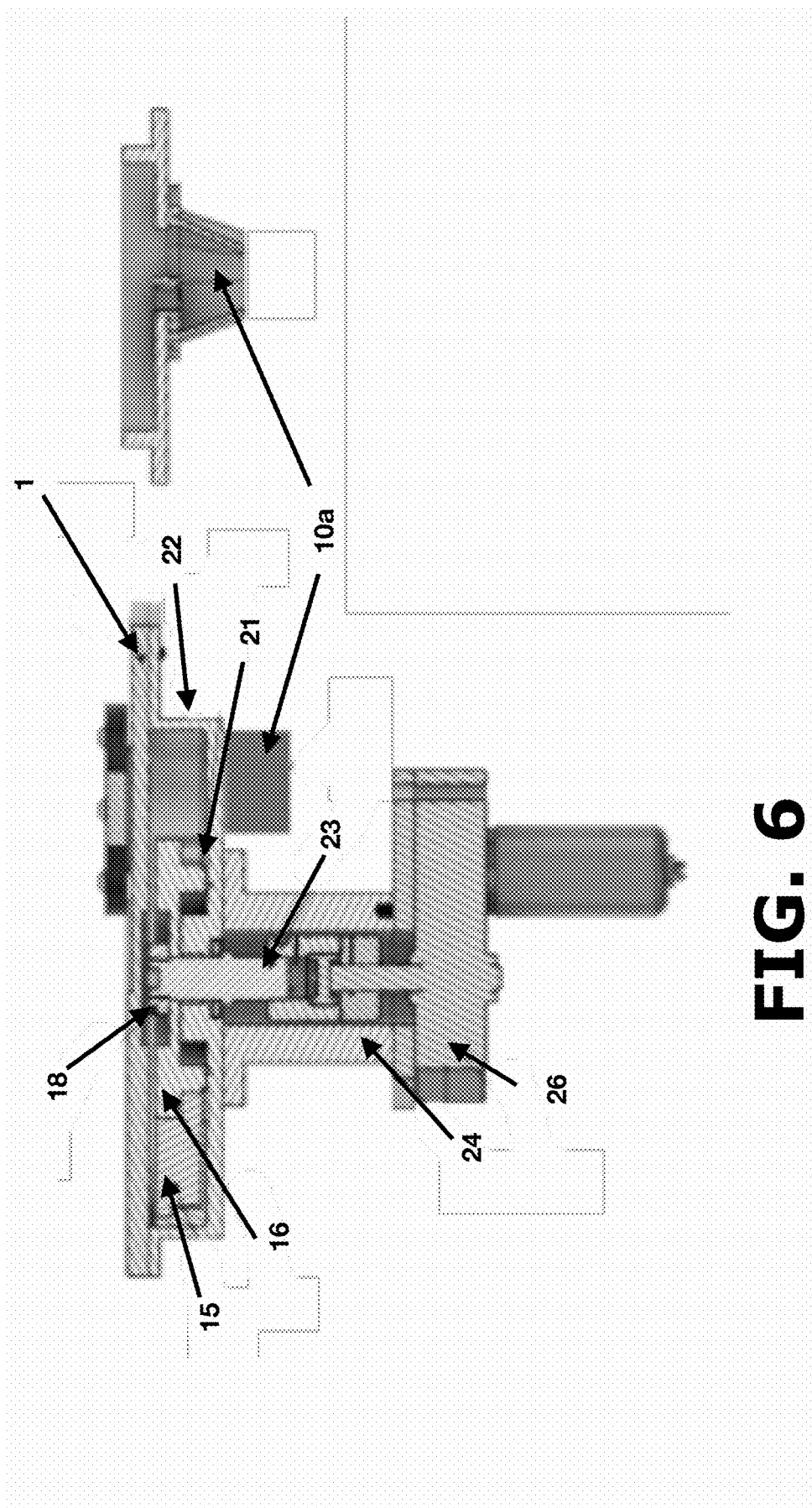
FIG. 6 shows a cross-sectional view of the powder sampler according to the present invention.
Figure 7:
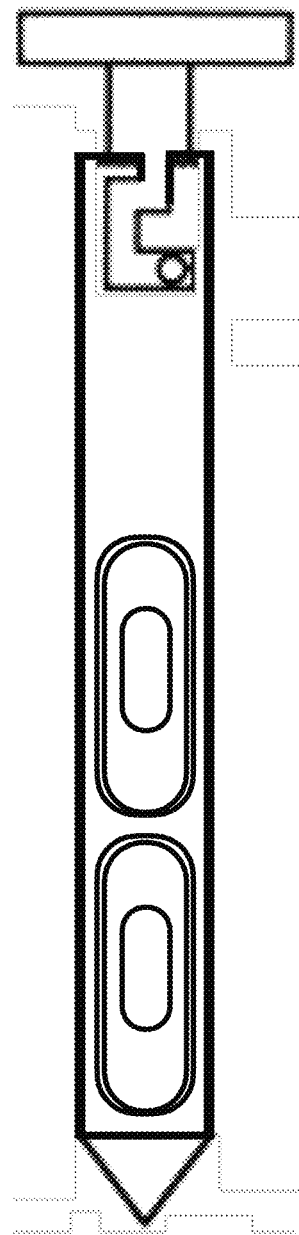
FIG. 7 illustrates a sample thief according to the prior art.
Figure 8:
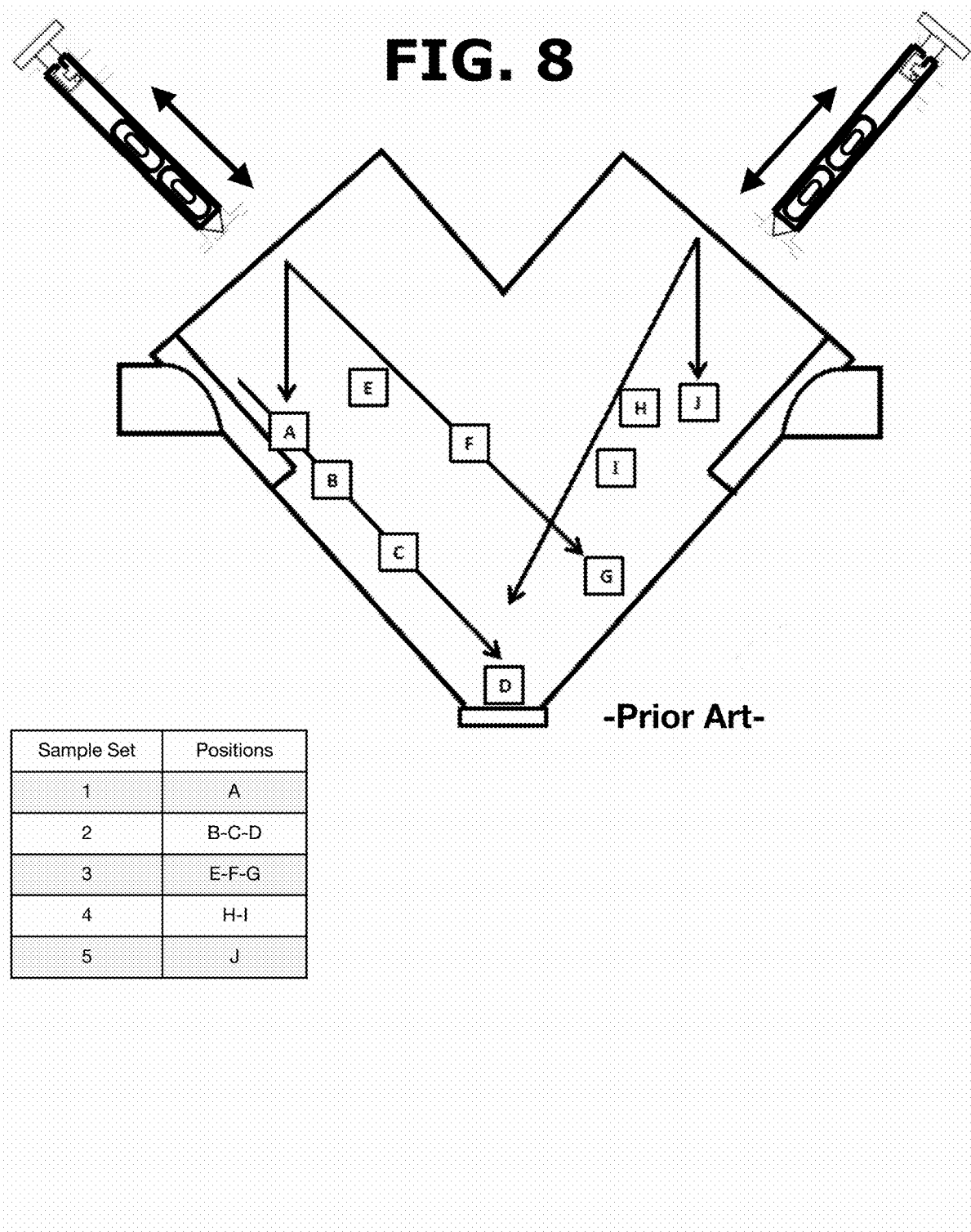
FIG. 8 illustrates a sampling procedure using a sample thief according to the prior art.

Powder entering the powder inlet (5) reaches into the powder flow area (9) shown on FIG. 3a. Once inside the powder flow area (9), the powder is distributed in the space between each paddle (15) as shown in FIG. 3b and reaches about 2 mm above the height of the paddles (15) so that there is no paddle related information in the spectroscopic measurements. Certain height tolerance and/or deviation are allowed or expected as long as there is no paddle related information in the spectroscopic measurements. FIG. 3b shows each paddle (15) removably connected to a paddle wheel hub (16) that is maintained in place by tightening a nut (18) to a device shaft adapter (17). The paddles (15) shown in FIG. 3b and FIG. 4 are coupled to the paddle wheel hub (16) by inserting a coupling end (15c) of said paddle into a receiving port (16a) of said wheel hub (16), wherein the combination of these two parts rotates counterclockwise the powder inside the powder flow area (9) shown in FIG. 3a. The paddles (15) comprise a stainless-steel paddle part (19) and a PTFE based Teflon® paddle seal (20) that covers the front portion (15a) and the base portion (15b) of each paddle (15) as shown in FIG. 4. The paddle (15) is designed to always be in contact with the base and the walls of the powder flow area (9) with minimal frictional forces as the PTFE (polytetrafluoroethylene) paddle seals (20) are well lubricated. The base of the powder flow area (9) contains an Acetal/PTFE Teflon® seal (21), as shown in FIG. 6, that further reduces the frictional forces between the base of the powder flow area (9) and the base of the paddles (15) which are also made from Teflon®. This arrangement is provided to avoid accumulation of powders in the base or walls of the powder flow area (9) avoiding any mixing of material while the paddles (15) are rotating. After rotation, the powder reaches the sampling system area (11) shown in FIG. 3a where a material sample can be obtained for making off-line measurements. The material sample is obtained in the sampling system area (11) in three steps. First, a container is inserted on a sampling port (13) of a removable sampling carrier (11a) outside of the powder flow area (9). Afterwards, the removable sampling carrier (11a) holding the container in the sampling port (13) is slowly inserted into the powder flow area (9) as shown in FIG. 3a. In this step, the sampling port (13) must be slowly moved to obtain a composite sample of several spaces between the paddles (15) constituting a more representative sample of the process happening inside the powder flow area (9). When the container is full, any excess powder flows through a sampling exit openings (12) to avoid powder accumulation in the removable sampling carrier (11a) and changes in the sampling size of the container. Finally, the removable sampling carrier (11a) is removed to collect the container with the desired sample. The sample size may be adjusted through the design of different sampling ports (13) and the weight of the off-line sample will change by selecting a die with a different volume. Regardless of this sampling process, powder ends up flowing through the device exit area (10) that is positioned about 270 degrees apart from the powder inlet (3). Certain distance tolerance and/or deviation are allowed or expected as long as proper sampling according to the principles of the present invention is performed before the powder exits the device. Device exit area (10) is provided to avoid any mixing of the material and to always have new material being analyzed eliminating the possibility of analyzing the same material again.

Figure 5:
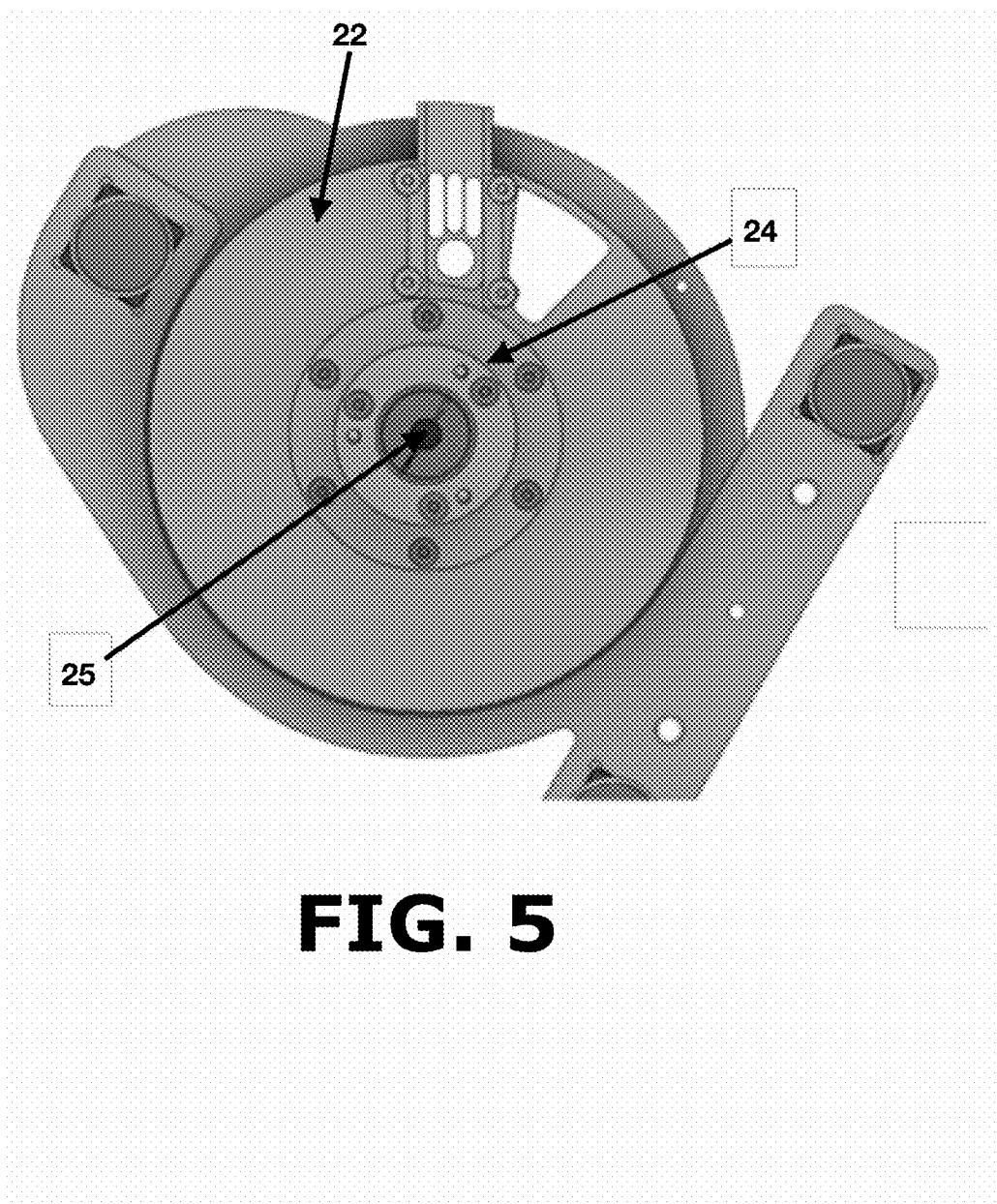
FIG. 5 shows a bottom view of the powder sampler according to the present invention.

FIG. 5 is a bottom view of the powder sampler of the present invention showing a motor adapter (24) and a motor shaft adapter (25) coupled to a bottom cover (22). FIG. 6 shows a cross-sectional view illustrating all the parts of the powder sampler. The top cover (1) coupled to its bottom cover (22), the paddles (15) positioned in direct contact with the Acetal/PTFE Teflon® Seal (21) and being connected to the paddle wheel hub (16) that is tightened to a drive shaft (23) with a nut (18). The drive shaft (23) is provided inside the motor adapter (25) and is connected to the nut (18) on the upper side and to a variable speed motor/transmission (26) on the lower side. Powder flow through the system will change proportionally to the change in paddle wheel speed controlled by the variable speed motor/transmission (26). Finally, powder flows out of the powder flow area (9) via the powder exit port (10a) where the exiting material is finally collected or directed to another part of a powder processing system.

The inventive device is designed to ensure that new material is constantly being sampled within the powder flow area (9), without mixing with previous sampled material. The system of the present invention was used and tested to sample a caffeine blend with excellent results. The Stream Sampler was tested through a series of run tests, which were then subsequently used to create a NIR calibration model to determine the caffeine concentration in mass reductions first location 1 and second location 2. According to the present invention, a mass reduction step occurs anytime during a process where the mass or amount of material to be sampled coming from a starting point having a defined mass is reduced to a smaller mass or amount of material for sampling purposes. A pharmaceutical product may consist of a batch of 500 kilograms. However, the entire 500 kg cannot be analyzed. The sampler is able to obtain a reduced mass through a systematic approach. For example, the sampler may be used by diverting 3 kg from the effluent of the blender towards the sample. This would be mass reduction 1. This material would then be analyzed through the sapphire window. The near infrared light transmitted through the sapphire window would interact with about 200 mg of the powder blend (mass reduction 2). Finally, the system could also be able to collect 100-900 mg of the powder blend which could be analyzed in an off-line laboratory (mass reduction 3). Mass reduction 3 would be especially useful for highly potent drugs, that have a low concentration in the formulation and are difficult to quantify accurately with near infrared spectroscopy in mass reduction 2.

Table 1 below shows the results using the inventive sampler to determine caffeine concentration by NIR spectroscopy, standard deviation, and relative standard deviation (% RSD) in mass reduction 2.

| Caffeine Blend Flowing through Stream Sampler (% w/w) | Mass reduction 2 NIR Spectroscopic Results Caffeine Concentration | | |
|---|---|---|---|
| | Avg. (% w/w) | Std. Dev. (% w/w) | RSD (%) |
| 11.50 | 11.61 | 0.31 | 2.67 |
| 13.99 | 14.12 | 0.37 | 2.62 |
| 15.00 | 15.08 | 0.40 | 2.65 |
| 16.49 | 16.42 | 0.40 | 2.44 |

The average caffeine concentration determined by NIR spectroscopy is generally within 0.1% (w/w) of the caffeine concentration in the blends prepared and sampled by the Stream Sampler of the present invention.

In an embodiment of the invention, mass reduction 3 comprises of a sample cup or carrier that collects a sample from the powder stream without interruption, wherein this sample may then be brought to an ultraviolet spectrometer or High-Performance Liquid Chromatographic System (HPLC) for analysis. In the sample tests that were run, the samples were successfully collected in the sample cup/container without interrupting powder flow.

As an important aspect of the invention, mass reduction 3 could be the only method to obtain information for potent drugs present at a very low drug concentration in powder blends. NIR spectroscopy lacks the sensitivity to analyze a number of potent drug formulations. Thus, potent drugs such as: ethinylestradiol or levoythyroxine formulations will likely require mass reduction 3 according to the present invention.

Table 2 below shows the average weight of each sample collected in nine different runs. The relative standard deviation of the powder blend weights collected was generally 1-2% (w/w), except in one run where it increased to 3.08% (w/w).

| Blend ID | Average Sample Weight (mg) | Std. Dev. Sample Weight | RSD % Sample Weight | UV-Vis Results (% w/w) | Standard Deviation (% w/w) | RSD (%) |
|---|---|---|---|---|---|---|
| 10.50 | 923.88 | 0.07721 | 1.47 | 10.44 | 0.6850 | 6.56 |
| 12.75 | 941.47 | 0.09705 | 1.25 | 12.88 | 0.7938 | 6.16 |
| 15.00 | 934.44 | 0.10993 | 1.27 | 14.70 | 0.4371 | 2.97 |
| 17.25 | 942.68 | 0.12411 | 1.00 | 16.46 | 0.9632 | 5.85 |
| 19.50 | 986.55 | 0.14536 | 3.08 | 18.44 | 1.5336 | 8.32 |
| 15.00 | 922.57 | 0.10103 | 1.01 | 13.71 | 1.1631 | 8.49 |
| 11.50 | 955.73 | 0.08945 | 1.22 | 11.70 | 0.5594 | 4.78 |
| 13.99 | 943.35 | 0.10532 | 1.37 | 13.95 | 0.5090 | 3.65 |
| 16.49 | 936.48 | 0.11946 | 1.32 | 15.95 | 0.8444 | 5.30 |
| Val_5 | 963.19 | 0.10775 | 1.47 | 13.98 | 1.2137 | 8.68 |

Four experiments were conducted where the results obtained by UV-Vis were compared with those of NIR spectroscopy (mass reduction 2). Table 3 below shows the comparison between the UV-Vis concentration predictions versus the NIR predictions using the second mass reductions step. The results obtained in sample reduction 2 were excellent (very close to the concentration of the caffeine blend).

| Caffeine Blend Flowing through Stream Sampler | Sample Reduction 3 NIR Spectroscopic Results Caffeine Concentration | | Sample Reduction 2 NIR Spectroscopic Results Caffeine Concentration | |
|---|---|---|---|---|
| Caffeine Blend Conc. % (w/w) | UV results Avg. % (w/w) | Std. Dev. (w/w) N = 17 | Avg. % (w/w) | Std. Dev. % (w/w) n = 230 |
| 11.50 | 11.70 | 0.56 | 11.61 | 0.31 |
| 13.99 | 13.95 | 0.51 | 14.12 | 0.37 |
| 15.00 | 13.71 | 1.16 | 15.08 | 0.40 |
| 16.49 | 15.95 | 0.84 | 16.42 | 0.40 |

Figure 9:
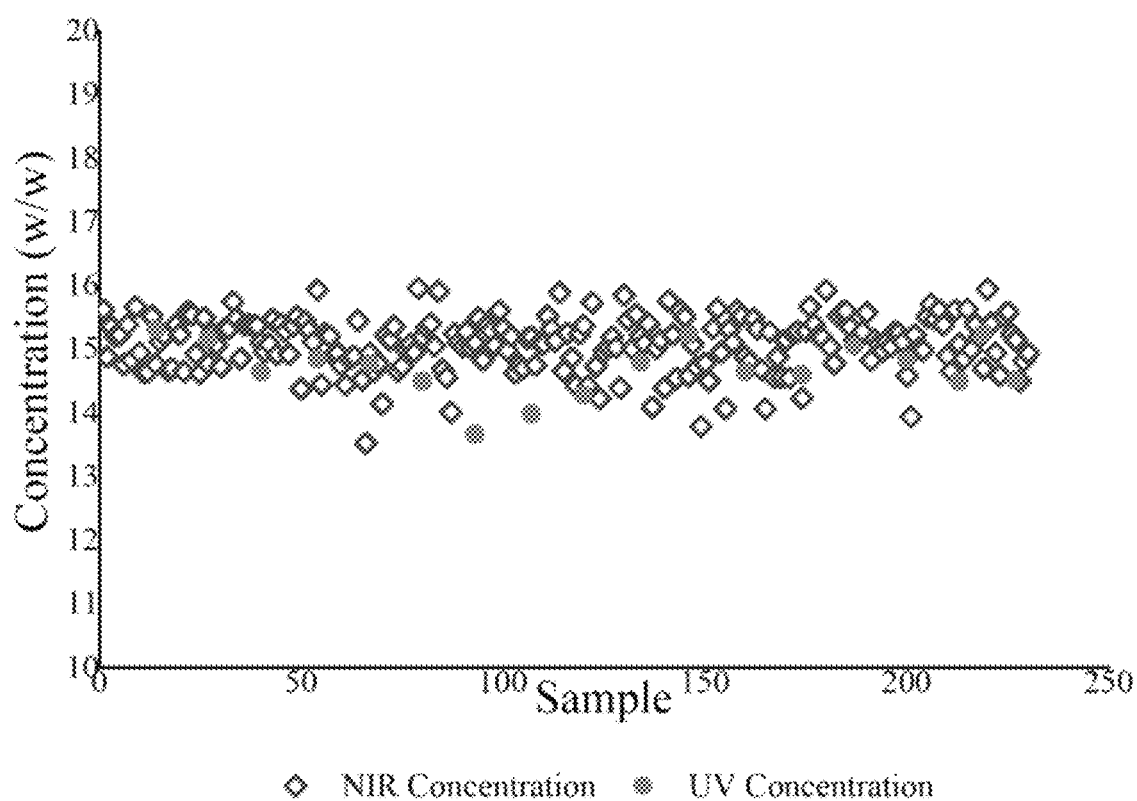
FIG. 9 shows caffeine concentration determined by NIR spectroscopy and UV-Vis spectroscopy according to the present invention.

FIG. 9 shows the caffeine concentration determined by NIR spectroscopy (mass reduction 2), and by UV-Vis spectroscopy (mass reduction 3). Blue diamonds represent NIR results and red circles represent UV results for the analysis of the 15.00% (w/w) blend after mass reductions 2 and 3 were performed. The results in the plot are in significant agreement between the results obtained in the two mass reductions. This close agreement was not expected since previous studies with continuous manufacturing equipment have shown differences between NIR and UV results.

As can be appreciated from FIG. 9, over 240 determinations of drug concentration were performed by NIR spectroscopy according to the present invention. These determinations were performed as the powder was flowing through mass reduction 2. In this case a total of 4.5 kg of the caffeine powder blend were analyzed every 5 seconds by NIR spectroscopy, and all parts of the batch had the same opportunity to be analyzed as recommended by the Fundamental Sampling Principle. The system of the present invention is an example of a 1-D sampling system implemented according to the Theory of Sampling. In a 1-D sampling system, there is always one specific dimension that is the most important for analysis purposes. In this case, time is the most important dimension as analyses are performed every 5 seconds. 1-D sampling makes it possible to use variographic analysis, which is an advantage of the stream sampler of the present invention.

The present invention will facilitate compliance with FDA expectations and regulations requiring the industry to clearly understand the sources of variation. The fact that multiple samples can be obtained facilitates the use of statistical methods to understand the sources of variation in the results obtained. The invention also facilitates variographic analysis, a statistical approach for the pharmaceutical industry. Variographic analysis requires knowing the order in which samples are obtained and the present invention allows to obtain this information from both batch and continuous mixing. Thus, the present invention will provide compliance with FDA expectation for rigorous statistical evaluation of the data obtained.

The powder sampler of the present invention is also sufficiently small allowing powder blends to be introduced into powder characterization instruments. In addition, the powder sampler of the present invention can be used to introduce powder to particle size distribution system such as the Insitec® by Malvern Instruments, or to an FT4 powder Rheometer® to provide valuable information on powder properties. However, their effectiveness depends on the powder samples received as Quality Control personnel could believe that the instrument is not working properly because the particle size results are too low. However, the problem could be that the sampling is favoring fine particle sizes. Accordingly, the present invention would be helpful to vendors of particle size distribution and characterization instruments, who often receive complaints that their instruments are not working well when in fact the problem is powder sampling. The present invention may be used to develop a batch or continuous manufacturing system, and then also for the subsequent validation in a pharmaceutical manufacturing site.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:

1. A sampling reduction system for flowing powders comprising:
   a powder inlet receiving and directing incoming powder into an enclosed circular powder flow area;
   a sampling window providing optical access of said enclosed circular powder flow area for real-time sampling of said powder;
   a plurality of paddles positioned inside said enclosed circular powder flow area and being provided to move said powder inside said enclosed circular powder flow area, wherein said plurality of paddles are coupled to a wheel hub centrally positioned inside said enclosed circular powder flow area;
   a powder exit area; and
   an off-line sampling area, provided on said enclosed circular powder flow area, having an off-line sampling opening configured to receive a removable sampling carrier holding a sample collection container.

2. The sampling reduction system of claim 1, wherein said off-line sampling area further comprises at least one sampling exit opening receiving excess powder from said sample collection container.

3. The sampling reduction system of claim 2, further comprising a powder exit port receiving exiting powder moved inside said enclosed powder flow area and the excess powder from said sample collection container.

4. The sampling reduction system of claim 1, wherein a base of said enclosed circular powder flow area comprises a base seal that reduces frictional forces between the base of said enclosed circular powder flow area and a base of said plurality of paddles.

5. The sampling reduction system of claim 1, further comprising a drive shaft coupled to said wheel hub for rotating said plurality of paddles.

6. The sampling reduction system of claim 5, wherein said drive shaft is also coupled to a variable speed motor/transmission system.

7. The sampling reduction system of claim 1, wherein said powder inlet further comprises:
   a powder line adapter configured to receive powder from an external source;
   a flexible adapter coupled to a lower end of said powder line adapter; and
   a cover adapter coupled between a lower end of said flexible adapter and an inlet of said enclosed circular powder flow area.

8. The sampling reduction system of claim 7, wherein said powder line adapter receives powder from at least one of: a pipe of an external powder processing system and an external stage of a sample reduction system.

9. The sampling reduction system of claim 7, wherein said flexible adapter is moved to adjust an angle of said powder inlet in relation to the inlet of said enclosed circular powder flow area.

10. The sampling reduction system of claim 1, wherein said sampling window is made from a material that allows mid and near infrared measurements.

11. The sampling reduction system of claim 1, wherein said sampling window is made from sapphire.

12. The sampling reduction system of claim 1, further comprising a mid and near infrared measuring instrument performing said real-time optical sampling of the powder via the sampling window.

13. The sampling reduction system of claim 1, wherein said powder inlet is positioned at a predetermined angular distance from a center of said sampling window.

14. The sampling reduction system of claim 1, wherein said powder inlet is positioned at about 200 degrees from a center of said sampling window.

15. The sampling reduction system of claim 1, wherein the powder inside said enclosed circular powder flow area is distributed in spaces between each paddle of said plurality of paddles and reaches a predetermined distance above the height of said plurality of paddles eliminating paddle related information from said real-time sampling of the powder.

16. The sampling reduction system of claim 15, wherein said predetermined distance is about 2 mm.

17. The sampling reduction system of claim 1, wherein said wheel hub comprises a plurality of receiving ports positioned around the periphery of said wheel hub and each paddle of said plurality of paddles comprises a coupling end removably inserted into a receiving port of said plurality of receiving ports.

18. The sampling reduction system of claim 1, wherein said plurality of paddles are rotated to move the powder inside the enclosed powder flow area in a counterclockwise direction.

19. The sampling reduction system of claim 1, wherein each paddle of said plurality of paddles comprises a solid paddle part and a polytetrafluoroethylene (PTFE) based paddle seal covering a front portion and a base portion of each paddle.

20. The sampling reduction system of claim 1, wherein said solid paddle part is made from stainless steel.

21. The sampling reduction system of claim 1, wherein said powder exit area is positioned at a predetermined angular distance from said powder inlet.

22. The sampling reduction system of claim 21, wherein said predetermined distance is about 270 degrees.

* * * * *